United States Patent
Masuda

(10) Patent No.: US 9,700,255 B2
(45) Date of Patent: Jul. 11, 2017

(54) CONSCIOUSNESS LEVEL DETERMINATION APPARATUS AND CONSCIOUSNESS LEVEL DETERMINATION METHOD

(75) Inventor: Yuta Masuda, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 946 days.

(21) Appl. No.: 13/310,111

(22) Filed: Dec. 2, 2011

(65) Prior Publication Data

US 2012/0071766 A1 Mar. 22, 2012

Related U.S. Application Data

(63) Continuation of application No. PCT/JP2009/070138, filed on Nov. 30, 2009.

(30) Foreign Application Priority Data

Jun. 4, 2009 (WO) .................. PCT/JP2009/060281

(51) Int. Cl.
*A61B 5/02* (2006.01)
*A61B 5/18* (2006.01)
(Continued)

(52) U.S. Cl.
CPC .............. *A61B 5/18* (2013.01); *A61B 5/0245* (2013.01); *A61B 5/02405* (2013.01); *A61B 5/4809* (2013.01)

(58) Field of Classification Search
CPC ....... A61B 5/18; A61B 5/0245; A61B 5/4809; A61B 5/02405
(Continued)

(56) References Cited

U.S. PATENT DOCUMENTS 6,126,595 A 10/2000 Amano et al.
6,890,304 B1 5/2005 Amano et al.
(Continued)

FOREIGN PATENT DOCUMENTS

EP 2087841 8/2009
EP 2092889 8/2009
(Continued)

OTHER PUBLICATIONS

Kamen et al., Poincare plot of heart rate variability allows quantitative display of parasympathetic nervous activity in humans, Clinical Science, 1996, vol. 91, pp. 201-208.*
(Continued)

*Primary Examiner* — Michael Kahelin
*Assistant Examiner* — Tho Tran
(74) *Attorney, Agent, or Firm* — Staas & Halsey LLP

(57) ABSTRACT

A consciousness level determination apparatus calculates a heart rate interval from a heart rate signal of a subject and calculates a spectral density of each frequency by performing a frequency analysis on the calculated heart rate interval. The apparatus extracts, at each predetermined timing, a combination of a maximum density that is a maximum, a maximum frequency that is a frequency corresponding to the maximum density, and a magnitude difference relation that represents a difference between the maximum density and spectrum densities which correspond to frequencies adjoined to the maximum frequency. The apparatus compares the combination with a combination extracted at a previous timing. The apparatus determines a consciousness level on the basis of a determination reference that is determined by using a result of the comparison.

5 Claims, 15 Drawing Sheets

(51) Int. Cl.
*A61B 5/024* (2006.01)
*A61B 5/0245* (2006.01)
*A61B 5/00* (2006.01)

(58) Field of Classification Search
USPC .............................. 600/481, 500–502, 508
See application file for complete search history.

(56) References Cited

U.S. PATENT DOCUMENTS

| | | | |
|---|---|---|---|
| 7,206,631 | B2 | 4/2007 | Kawachi et al. |
| 2002/0013533 | A1 | 1/2002 | Oka et al. |
| 2004/0243013 | A1 | 12/2004 | Kawachi et al. |

FOREIGN PATENT DOCUMENTS

| | | |
|---|---|---|
| JP | 8-299443 | 11/1996 |
| JP | 2004-350773 | 12/2004 |
| JP | 2006-158733 | 6/2006 |
| JP | 2008-140156 | 6/2008 |
| WO | 2008/065724 | 6/2008 |
| WO | 2008/069337 | 6/2008 |
| WO | 2009/020074 | 2/2009 |

OTHER PUBLICATIONS

International Search Report, mailed Feb. 23, 2010, in corresponding International Application No. PCT/JP2009/070138 (5 pp.).
Form PCT/ISA/237, mailed Feb. 23, 2010, in corresponding International Application No. PCT/JP2009/070138.
European Office Action issued Nov. 29, 2012 in corresponding European Patent Application No. 09845555.3.

* cited by examiner

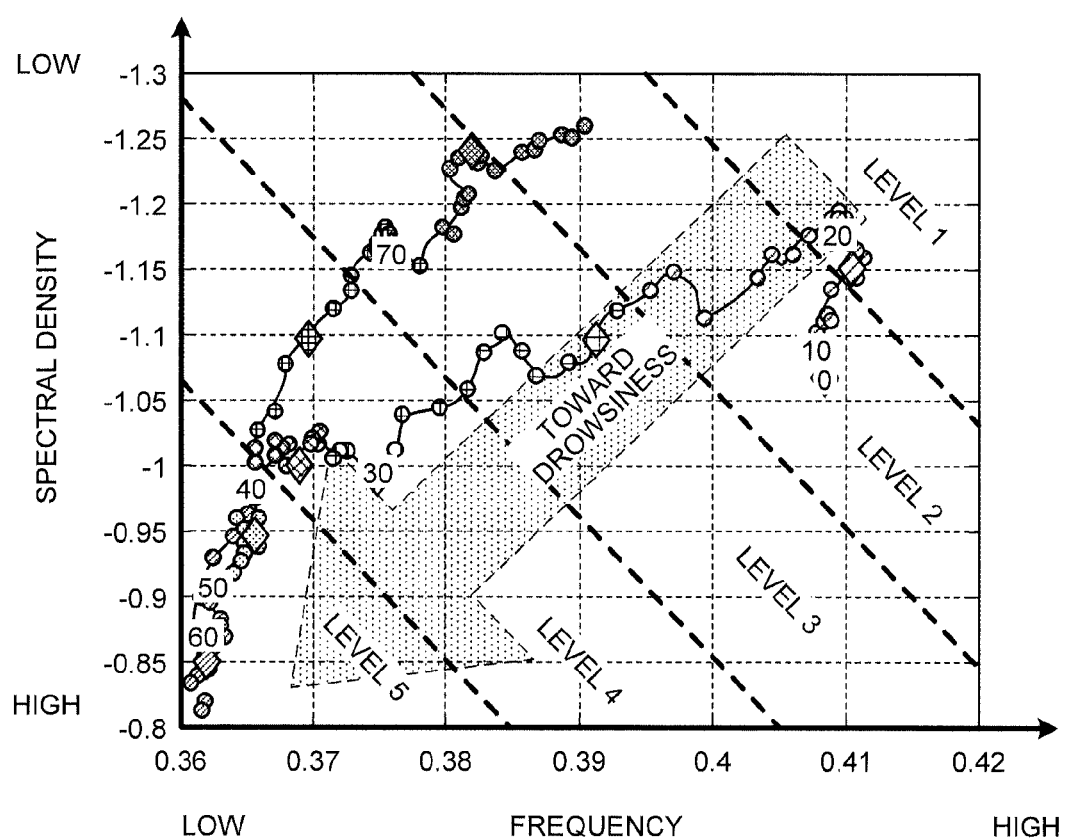

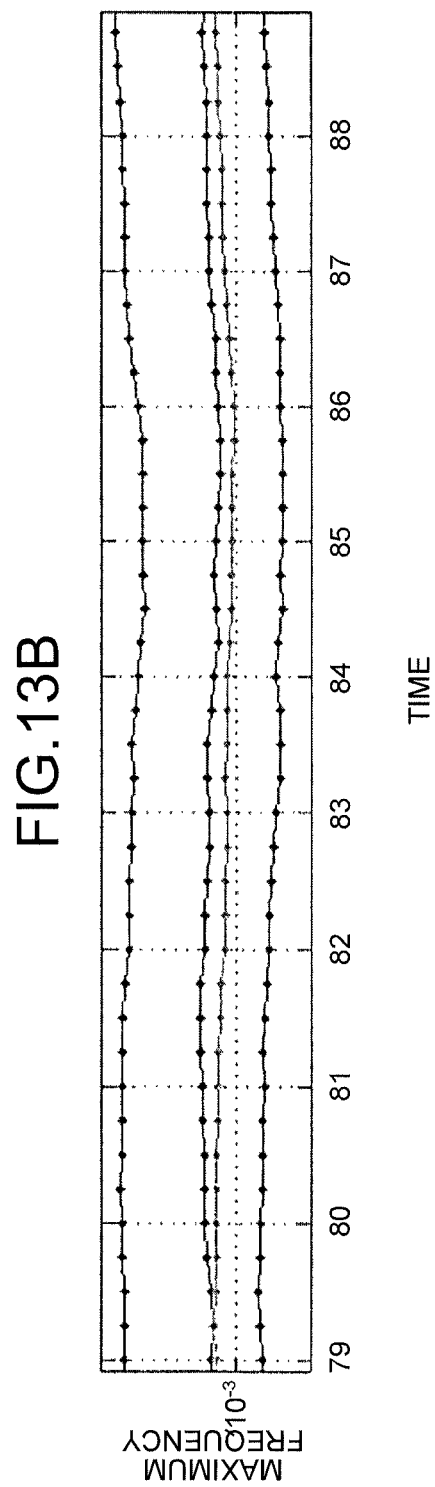

CONSCIOUSNESS LEVEL DETERMINATION APPARATUS AND CONSCIOUSNESS LEVEL DETERMINATION METHOD

CROSS-REFERENCE TO RELATED APPLICATIONS

This application is a continuation of International Application No. PCT/JP2009/070138, filed on Nov. 30, 2009, which claims the benefit of priority of the prior International Application No. PCT/JP2009/060281, filed on Jun. 4, 2009, the entire contents of which are incorporated herein by reference.

FIELD

The present invention relates to a consciousness level determination apparatus, a consciousness level determination method, and a consciousness level determination program.

BACKGROUND

As conventional methods of measuring the drowsiness and consciousness level of a subject without putting pressure on the subject, the method using the heart rate or a pulse wave signal are known. For example, a method is known in which the peak frequency of a heart rate signal during consciousness is used as a reference and the drowsiness level of a subject is evaluated according to whether the frequency of the heart rate signal of the subject is lower than the peak frequency. Furthermore, for example, a method is also known in which the consciousness level of a subject is evaluated according to the intensity of a low frequency part or a high frequency part of a pulse wave signal or the ratio between the low frequency part and the high frequency part.
Patent Document 1: Japanese Laid-open Patent Publication No. 2004-350773
Patent Document 2: Japanese Laid-open Patent Publication No. 8-299443

SUMMARY

According to an aspect of an embodiment of the invention, a consciousness level determination apparatus includes an interval calculator that calculates a heart rate interval from a heart rate signal of a subject. The consciousness level determination apparatus includes a spectrum calculator that calculates a spectral density of each frequency by performing a frequency analysis on the heart rate interval. The heart rate interval is calculated by the interval calculator. The consciousness level determination apparatus includes an extraction unit that extracts, at each predetermined timing, a combination of a maximum density that is a maximum among spectral densities that are calculated by the spectrum calculator, a maximum frequency that is a frequency corresponding to the maximum density, and a magnitude difference relation that represents a difference between the maximum density and spectrum densities which correspond to frequencies adjoined to the maximum frequency. The consciousness level determination apparatus includes a comparison unit that compares the maximum frequency, the maximum density, and the magnitude difference relation, which are contained in the combination extracted by the extraction unit, with a maximum frequency, a maximum density, and a magnitude difference relation that are contained in a combination extracted at a previous timing. The consciousness level determination apparatus includes a determination unit that determines a consciousness level on the basis of a determination reference that is determined by using a result of the comparison performed by the comparison unit.

The object and advantages of the embodiment will be realized and attained by means of the elements and combinations particularly pointed out in the claims.

It is to be understood that both the foregoing general description and the following detailed description are exemplary and explanatory and are not restrictive of the embodiment, as claimed.

BRIEF DESCRIPTION OF DRAWINGS

FIG. 8 is a diagram illustrating the allocation of drowsiness levels to areas of the graph that is performed by the consciousness level determination adjuster of the second embodiment;

FIG. 13B is a diagram of changes in maximum density in the time series in the second embodiment;

DESCRIPTION OF EMBODIMENTS

In the above-described conventional methods, however, there is a problem in that, in a state where the subject feels drowsy but is resisting falling asleep, the consciousness level cannot be determined. Specifically, in a state where the subject feels drowsy but is resisting falling asleep, the heart rate signal indicates changes that are different from changes during a normal shift to sleep, and therefore the drowsiness level of the subject cannot be determined.

Embodiments of a consciousness level determination apparatus, a consciousness level determination method, and a consciousness level determination program will be described in detail below with reference to the accompanying drawings.

[a] First Embodiment

Figure 1:
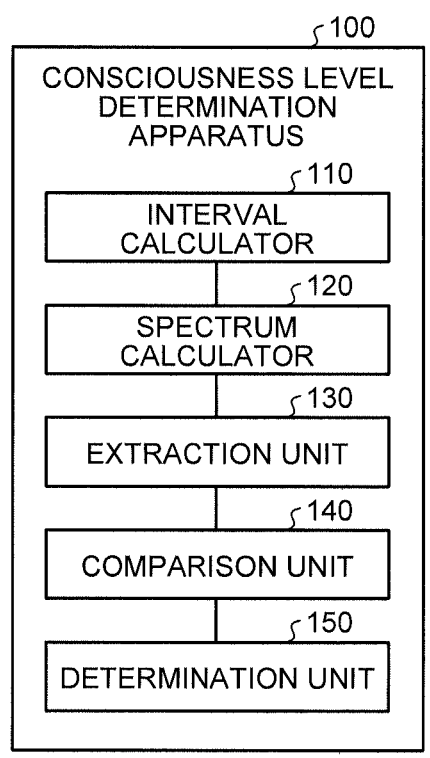
FIG. 1 is a block diagram illustrating an example of a configuration of a consciousness level determination apparatus according to a first embodiment.

Configuration of Consciousness Level Determination Apparatus According to First Embodiment An example of a configuration of a consciousness level determination apparatus 100 according to a first embodiment will be described using FIG. 1. FIG. 1 is a block diagram illustrating an example of the configuration of the consciousness level determination apparatus according to the first embodiment.

As illustrated in FIG. 1, the consciousness level determination apparatus 100 according to the first embodiment includes an interval calculator 110, a spectrum calculator 120, an extraction unit 130, a comparison unit 140, and a determination unit 150.

The interval calculator 110 calculates a heart rate interval from a heart rate signal of a subject. The spectrum calculator 120 calculates the spectral density of each frequency by performing a frequency analysis on the heart rate interval that is calculated by the interval calculator 110.

The extraction unit 130 extracts, at each timing, a combination of a maximum density that is a maximum among spectral densities that are calculated by the spectrum calculator 120, a maximum frequency that is a frequency corresponding to the maximum density, and a magnitude difference relation.

The magnitude difference relation represents the difference between the spectral densities, which correspond to the frequencies before and after the maximum frequency, and the maximum density. For example, in a heart rate spectrum in which the horizontal axis represents frequency and the vertical axis represents the spectral density, the sharper the shape of the peak corresponding to the maximum, the larger the difference becomes between the spectral densities, which correspond to the frequencies before and after the maximum frequency, and the maximum density. The more gentle the shape of the peak corresponding to the maximum, the smaller the difference becomes between the spectral densities, which correspond to the frequencies before and after the maximum frequency, and the maximum density.

The comparison unit 140 compares the maximum frequency, the maximum density, and the magnitude difference relation that are contained in the combination, which is extracted by the extraction unit 130, with a maximum frequency, a maximum density, and a magnitude difference relation, respectively, that are contained in a combination extracted at a previous timing.

The determination unit 150 determines a consciousness level on the basis of a determination reference that is determined according to the result of the comparison by the comparison unit 140. Specifically, the determination unit 150 determines that the consciousness level decreases when, as a result of the comparison by the comparison unit 140, a comparison result is obtained that indicates that the maximum frequency has decreased, the maximum density has decreased, and the magnitude difference relation has decreased compared to the combination extracted at the previous timing.

Effects of First Embodiment

As described above, according to the first embodiment, the consciousness level determination apparatus 100 can determine a consciousness level even if a subject feels drowsy but is in a state of resisting falling asleep.

[b] Second Embodiment

Figure 2:
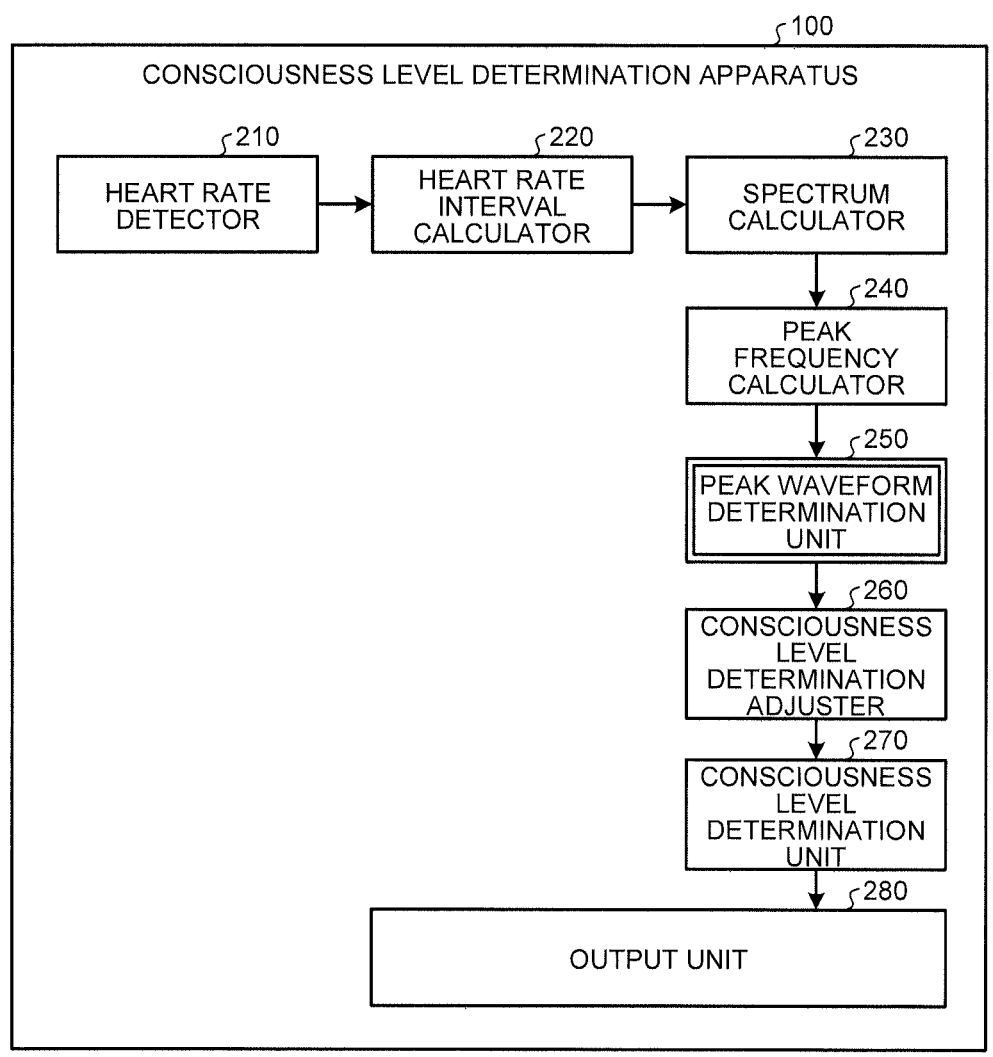
FIG. 2 is a block diagram illustrating an example of a configuration of a consciousness level determination apparatus according to a second embodiment.

Configuration of Consciousness Level Determination Apparatus According to Second Embodiment An example of a configuration of the consciousness level determination apparatus 100 according to a second embodiment will be described using FIG. 2. FIG. 2 is a block diagram illustrating an example of the configuration of the consciousness level determination apparatus according to the second embodiment.

As illustrated in FIG. 2, the consciousness level determination apparatus 100 includes a heart rate detector 210, a heart rate interval calculator 220, a spectrum calculator 230, a peak frequency calculator 240, a peak waveform determination unit 250, a consciousness level determination adjuster 260, a consciousness level determination unit 270, and an output unit 280.

The heart rate detector 210 and the heart rate interval calculator 220 among the units represented in FIG. 2 correspond to the interval calculator 110 in FIG. 1. The spectrum calculator 230 and the peak frequency calculator 240 correspond to the spectrum calculator 120 and the extraction unit 130, respectively. The peak waveform determination unit 250 corresponds to the comparison unit 140 in FIG. 1. The consciousness level determination adjuster 260 and the consciousness level determination unit 270 correspond to the determination unit 150 in FIG. 1.

Figure 3:
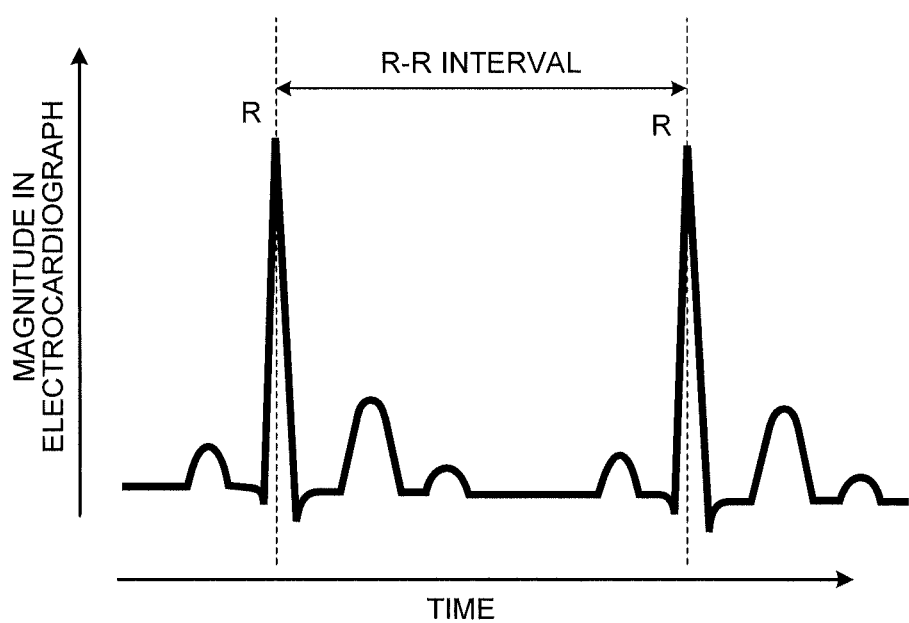
FIG. 3 is a diagram of an example of a heart rate signal that a heart rate detector of the second embodiment detects.

The heart rate detector 210 is connected to the heart rate interval calculator 220. As illustrated in FIG. 3, the heart rate detector 210 detects a heart rate signal of the subject. For example, the heart rate detector 210 applies a voltage to an electrode that makes contact with the subject and acquires a heart rate signal from the subject by using the potential difference of each electrode. FIG. 3 is a diagram of an example of the heart rate signal that is detected by the heart rate detector of the second embodiment. The horizontal axis in FIG. 3 represents the elapse of time and the vertical axis represents the magnitude of an electrocardiogram. The subject is, for example, a driver who is driving a two-wheel automotive vehicle or a four-wheel automotive vehicle. The electrodes used by the heart rate detector 210 are embedded in the steering wheel or steering bar of a two-wheel automotive vehicle or a four-wheel automotive vehicle.

The heart rate detector 210 outputs the detected heart rate signal to the heart rate interval calculator 220. For example, the heart rate detector 210 outputs the heart rate signal illustrated in FIG. 3.

The heart rate interval calculator 220 is connected to the heart rate detector 210 and the spectrum calculator 230. The heart rate interval calculator 220 receives a heart rate signal from the heart rate detector 210, detects an amplitude peak of the heart rate signal on the basis of the received heart rate signal, and calculates a heart rate interval that is the timing interval between each detection.

A heart rate interval calculation process performed by the heart rate interval calculator 220 will be further described using FIG. 3. As illustrated using "R" in FIG. 3, the heart rate interval calculator 220 detects amplitude peaks from the heart rate signal, which is received from the heart rate detector 210. Specifically, the heart rate interval calculator 220 detects amplitude peaks of the heart rate signal that are equal to or greater a threshold. Furthermore, as illustrated using "R-R interval" in FIG. 3 represents, the heart rate interval calculator 220 calculates the heart rate interval by calculating the interval between the detected amplitude peaks "R".

The method of detecting an amplitude peak is not limited to the above-described method. For example, it is possible to use a method that uses a zero cross point where the derivative of the heart rate signal changes from positive to negative or a method of detecting peaks by performing a pattern matching on the amplitude waveform.

The heart rate interval calculator 220 outputs the calculated heart rate interval to the spectrum calculator 230. For example, the heart rate interval calculator 220 calculates a heart rate interval each time it detects a new amplitude peak and outputs the calculated heart rate interval to the spectrum calculator 230.

Figure 4:
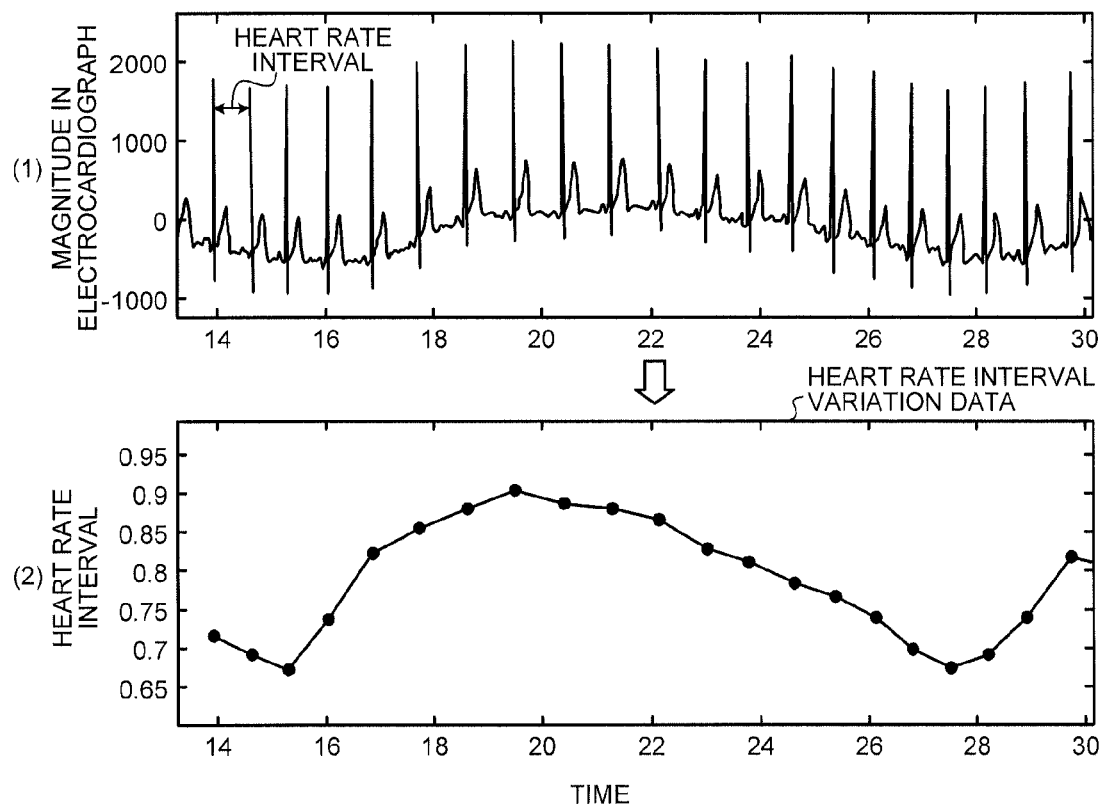
FIG. 4 is a diagram of heart rate interval variation data in the second embodiment, which is data represented on a graph as the heart rate interval-time plane.

The spectrum calculator 230 is connected to the heart rate interval calculator 220 and the peak frequency calculator 240. The spectrum calculator 230 receives a heart rate interval from the heart rate interval calculator 220 and calculates, on the basis of the received heart rate intervals, heart rate interval variation data that represents changes in the heart rate interval in accordance with the elapse of time, illustrated in FIG. 4(2). FIG. 4 is a diagram of heart rate interval variation data in the second embodiment, which is data represented on a graph as the heart rate interval-time plane.

FIG. 4 will be described briefly. FIG. 4(2) is a diagram of heart rate interval variation data of the second embodiment on the graph as the heart rate interval-time plane, where the horizontal axis represents the elapse of time and the vertical axis represents the heart rate interval. For reference, a diagram clearly illustrating the heart rate intervals on the diagram representing the heart rate signal, which is detected by the heart rate detector 210, is represented by FIG. 4(1). In FIG. 4(1), the horizontal axis represents the elapse of time and the vertical axis represents the magnitude of an electrocardiogram.

Figure 5:
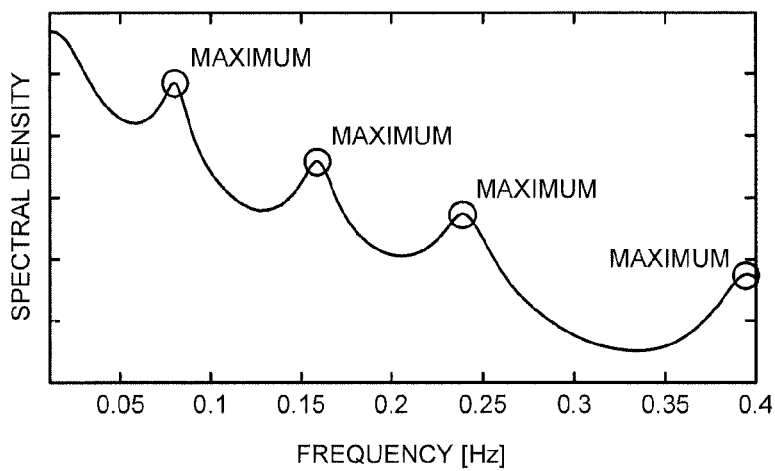
FIG. 5 is a diagram of an example of the relation between frequency and spectral density in the second embodiment.
Figure 6:
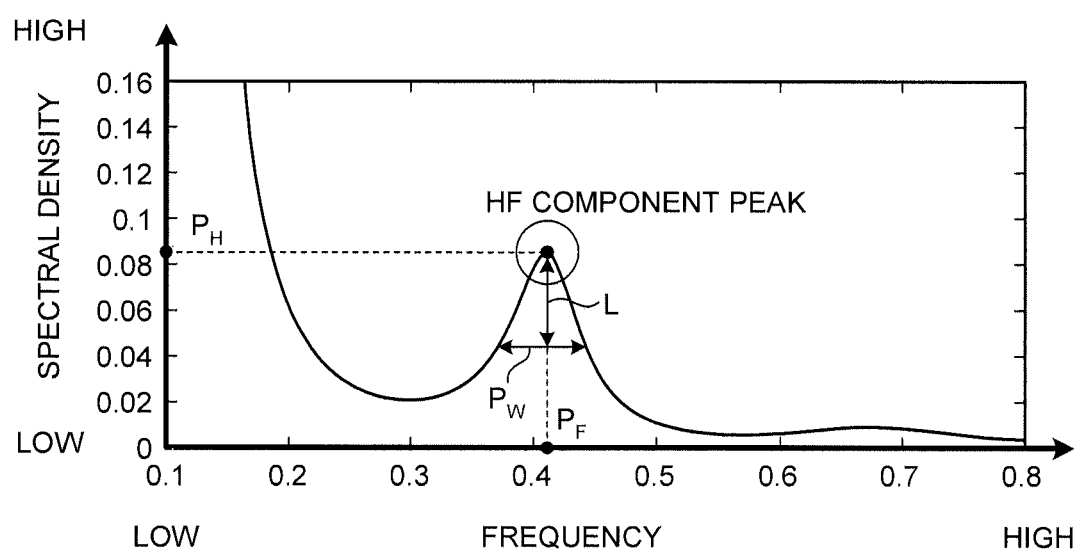
FIG. 6 is a diagram of an example of the relation between frequency and spectral density in the second embodiment.

The spectrum calculator 230 calculates the spectral density of each frequency, as illustrated in FIG. 5, by performing a frequency analysis on the heart rate interval variation data. In other words, spectral density data representing the relation between the spectral density and the frequency is calculated. FIG. 5 is a diagram of an example of the relation between frequency and spectral density. Regarding the example illustrated in FIG. 5, an example is illustrated in which multiple maxima are in an HF component (0.15 to 0.5 Hz) that reflects the state of the parasympathetic nerve. However, for example, there may be one maximum in the HF component, as illustrated in FIG. 6.

Furthermore, the spectrum calculator 230 outputs the spectral density data to the peak frequency calculator 240. For example, the spectrum calculator 230 calculates spectral density data each time it receives a new heart rate interval from the heart rate interval calculator 220. The spectrum calculator 230 then outputs the calculated spectral density data to the peak frequency calculator 240.

The method with which the spectrum calculator 230 calculates a spectral density of each frequency will be further described. The spectrum calculator 230 can calculate a spectral density by using any method. For example, the spectrum calculator 230 calculates a spectral density using an auto regressive (AR) model. As disclosed in a non-patent document (Syunsuke Sato, Akira Yoshida, Toru Kiryu "Fundamentals of Biological Signal Processing", Corona), the AP model is a model that represents the state at a certain time point by using a linear sum of old time series data. The AR model has a characteristic in that a clear maximum can be obtained by using a small volume of data compared with when a Fourier transformation is used.

The following AP model of order P of time series x(s) is given by $$x(s) = \sum_{m=1}^{p} a(m)x(s-m) + e(s) \quad (1)$$

using an AP coefficient a(m) and an error term e(s). Ideally, e(s) is white noise.

If p is the identifying order, $f_s$ is the sampling frequency, $\epsilon_p$ is the identifying error, and $\hat{a}_p(k)$ is an AR coefficient of order k, the spectral density $P_{AR}(f)$ is given by the following equation.

$$P_{AR}(f) = \frac{1}{f_s} \frac{\varepsilon_p}{\left|1 + \sum_{k=1}^{p} \hat{a}_p(k)e^{\frac{-2\pi jkf}{f_k}}\right|^2} \quad (2)$$

The spectrum calculator 230 calculates spectral density data according to Equation (2) and the heart rate interval variation data.

As illustrated in FIG. 2, the peak frequency calculator 240 is connected to the spectrum calculator 230 and the peak waveform determination unit 250. The peak frequency calculator 240 receives the spectral density data from the spectrum calculator 230 and, each time it receives spectral density data, extracts a combination of a maximum density, a maximum frequency, and a magnitude difference relation.

Specifically, each time the peak frequency calculator 240 receives spectral density data like that in FIG. 6, it extracts a combination of the "maximum density" denoted by "$P_H$" in FIG. 6, the maximum frequency denoted by "$P_F$", and the magnitude difference relation denoted by "$P_W$" in FIG. 6. FIG. 6 is a diagram of an example of the relation between frequency and spectral density in the second embodiment in which one maximum density is in the HF component.

The method with which the peak frequency calculator 240 extracts a magnitude difference relation and a method with which the peak frequency calculator 240 extracts a maximum density and a maximum frequency will be further described. First, the method of extracting a magnitude difference relation will be described and then the method of extracting a maximum density and a maximum frequency will be described below. The methods used by the peak frequency calculator 240 for the extraction are not limited to the methods described below and other methods may be used.

The method with which the peak frequency calculator 240 extracts a magnitude difference relation will be further described. As illustrated using "$P_W$" in FIG. 6, the peak frequency calculator 240 acquires, as a magnitude difference relation, a value of a width of a spectral waveform at a predetermined length "L" from a maximum. Frequencies specified by "$P_W$", i.e., frequencies in a case where the spectrum density is less than "$P_H$" by "L" and that are less than or greater than "$P_F$", correspond to the frequencies before and after the maximum frequency.

The length "L" is a pre-set value and the peak frequency calculator 240 always uses the same "L". The zero cross point at which the differential coefficient of the spectral waveform changes from positive to negative may be set as the baseline and the value of the segment thus obtained may be set as a magnitude difference relation.

The method with which the peak frequency calculator 240 extracts a maximum density and a maximum frequency will be further described. For example, the peak frequency calculator 240 calculates the frequency f satisfying $$\frac{dP_{AR}(f)}{df} = 0 \qquad (3)$$

as a maximum frequency and calculates a maximum density by substituting the maximum frequency to Equation (2).

The peak frequency calculator 240 outputs a combination of the maximum density, the maximum frequency, and the magnitude difference relation to the peak waveform determination unit 250. For example, with respect to each received spectral density data, a combination of a maximum density, a maximum frequency, and a magnitude difference relation is extracted and the combination is output to the peak waveform determination unit 250.

The peak waveform determination unit 250 is connected to the peak frequency calculator 240 and the consciousness level determination adjuster 260. The peak waveform determination unit 250 receives the combination of the maximum frequency, the maximum density, and the magnitude difference relation from the peak frequency calculator 240. The peak waveform determination unit 250 compares the maximum frequency, the maximum density, and the magnitude difference relation of the received combination with a maximum frequency, a maximum density, and a magnitude difference relation of a combination that is calculated by the peak frequency calculator 240 prior to the received combination.

The maximum frequency, the maximum density, and the magnitude difference relation that are contained in the received combination are referred below to as a received maximum frequency, a received maximum density, and a received magnitude difference relation, respectively. Furthermore, the combination that is calculated prior to the received combination is referred to as an old combination and the maximum frequency, the maximum density, and the magnitude difference relation that are contained in the old combination are referred to as an old maximum frequency, an old maximum density, and an old magnitude difference relation.

The above-described old combination corresponds to, for example, the combination that is calculated at a timing just before the timing at which the received combination was calculated by the peak frequency calculator 240.

Back to the description of the peak waveform determination unit 250. The peak waveform determination unit 250 compares the received maximum frequency and the old maximum frequency and determines whether the received maximum frequency is equal to or less than the old maximum frequency. The peak waveform determination unit 250 also compares the received maximum density and the old maximum density and determines whether the received maximum density is equal to or greater than the old maximum density. The peak waveform determination unit 250 compares the received magnitude difference relation and the old magnitude difference relation and determines whether the received magnitude difference relation is equal to or greater than the old magnitude difference relation.

The results of the comparison performed by the peak waveform determination unit 250 are used by the consciousness level determination adjuster 260. Specifically, the results are information for determining whether the subject is in a state where he/she feels drowsy but is resisting falling asleep.

The peak waveform determination unit 250 adds the results of the comparison to the received maximum frequency and the received maximum density, which are received from the peak frequency calculator 240, and outputs it to the consciousness level determination adjuster 260.

The consciousness level determination adjuster 260 is connected to the peak waveform determination unit 250 and the consciousness level determination unit 270. As described below, the consciousness level determination adjuster 260 plots the combination of the received maximum frequency and the received maximum density on a consciousness level determination graph where the axes represents spectral density and frequency, divides the area of the consciousness level determination graph, and allocates the divided areas with drowsiness levels.

Figure 7:
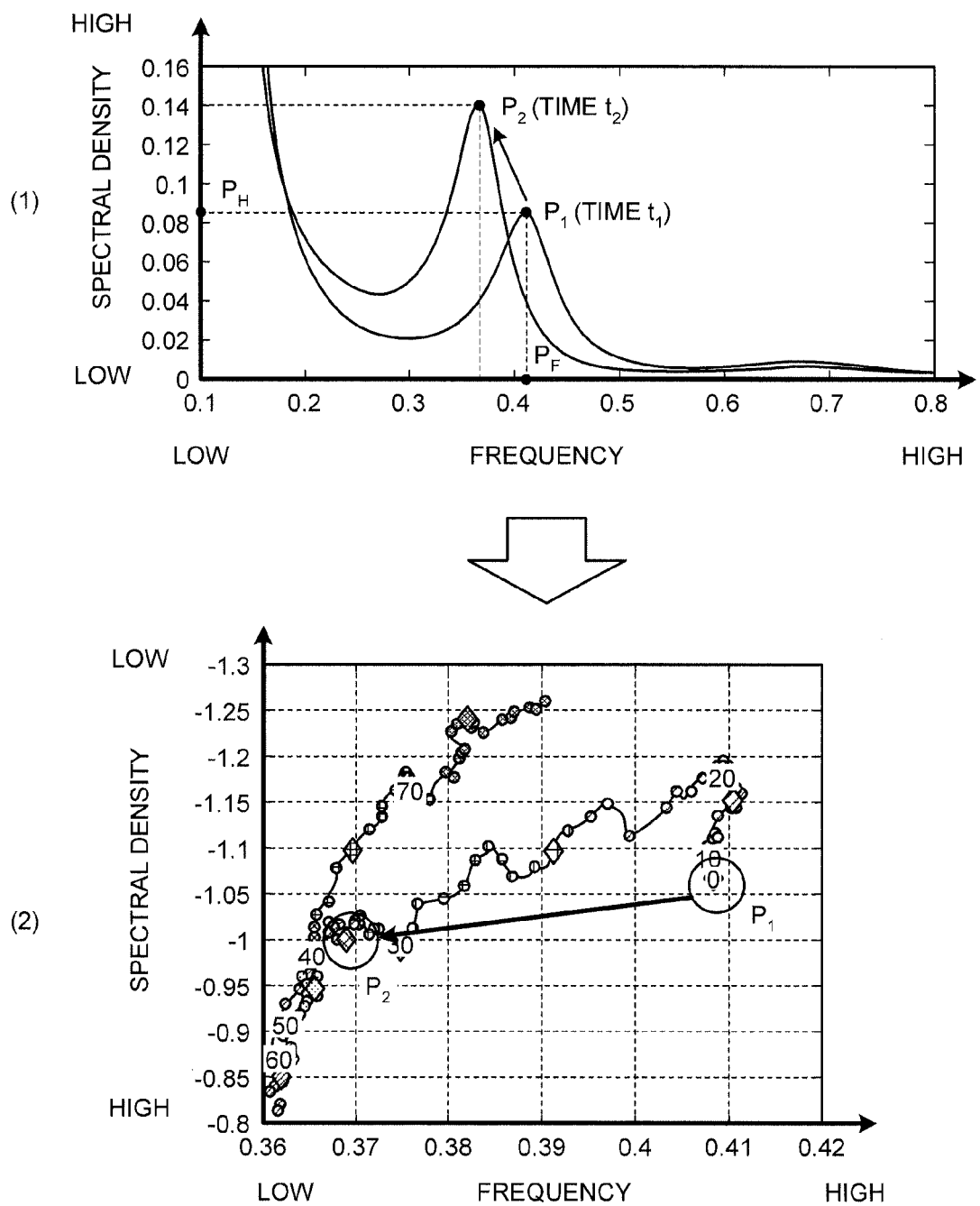
FIG. 7 is a diagram illustrating the plotting of a graph that is performed by a consciousness level determination adjuster of a second embodiment.

Plotting of the consciousness level determination graph will be described here. The consciousness level determination adjuster 260 receives the received maximum frequency, the received maximum density, and the comparison results from the peak waveform determination unit 250. As depicted in FIG. 7(2), the consciousness level determination adjuster 260 then plots the combination of the spectral density and the frequency on the consciousness level determination graph, where the axes represent spectral density and frequency, by using the method corresponding to the comparison results. FIG. 7 is a diagram illustrating plotting on the graph, which is performed by the consciousness level determination adjuster of the second embodiment. FIG. 7(1) corresponds to spectral density data from which "P1" and "P2" in the graph of FIG. 7(2) are calculated.

The description will be given under the assumption that, in the consciousness level determination graph to which the combination of the maximum frequency and the maximum density are plotted, the spectral density becomes lower toward the top and the frequency becomes higher toward the right in the area of the consciousness level determination graph.

Plotting on the consciousness level determination graph by using the method corresponding to the comparison results will be described after the allocation of drowsiness levels is described.

Allocation of drowsiness levels is described here. The consciousness level determination adjuster 260 adjusts the scale of the consciousness level determination graph and, as illustrated in FIG. 8, the consciousness level determination adjuster 260 divides the area of the consciousness level determination graph into five areas from the upper right to the lower left and allocates drowsiness levels of "five" levels to the five areas, respectively. FIG. 8 is a diagram illustrating allocation of the drowsiness levels to the areas of the consciousness level determination graph, which is an allocation performed by the consciousness level determination adjuster of the second embodiment.

For example, the consciousness level determination adjuster 260 allocates the drowsiness levels "1" to "5" sequentially from the upper right to lower left areas. The drowsiness level increases from "1" to "5", indicating how the consciousness level is low. The drowsiness level is used by the consciousness level determination unit 270, which will be described below.

Adjustment to the scale of the consciousness level determination graph will be further described. The consciousness level determination adjuster 260 detects the highest point, the lowest point, the rightmost point, and the leftmost point. The highest point is a point with the largest spectral density among the plotted points on the consciousness level determination graph. The lowest point is a point with the smallest spectral density among the plotted points on the consciousness level determination graph. The rightmost point is a point with the highest frequency among the plotted points on the consciousness level determination graph. The leftmost point is a point with the lowest frequency among the plotted points on the consciousness level determination graph. The plotted points on the consciousness level determination graph are different depending on the subject. Accordingly, the highest point, the lowest point, the rightmost point, and the leftmost point, which are detected by the consciousness level determination adjuster 260, are different depending on the subject.

The consciousness level determination adjuster 260 adjusts the scale of the consciousness level determination graph such that the detected highest point, the lowest point, the rightmost point, and the leftmost point are optimally contained in the consciousness level determination graph. For example, the consciousness level determination adjuster 260 adjusts the scale of the consciousness level determination graph such that the minimum value of frequency contained in the consciousness level determination graph is the frequency obtained by subtracting a predetermined value from the frequency of the leftmost point. The consciousness level determination adjuster 260 adjusts the scale of the consciousness level determination graph such that the maximum value of frequency contained in the consciousness level determination graph is a frequency obtained by adding a predetermined value to the frequency of the rightmost point. For example, the consciousness level determination adjuster 260 adjusts the scale of the consciousness level determination graph such that the minimum value of the spectral density contained in the consciousness level determination graph is a spectral density obtained by subtracting a predetermined value from the spectral density of the lowest point. For example, the consciousness level determination adjuster 260 adjusts the scale of the consciousness level determination graph such that the maximum value of the spectral density contained in the consciousness level determination graph is a spectral density obtained by adding a predetermined value to the spectral density of the highest point.

Figure 9A:
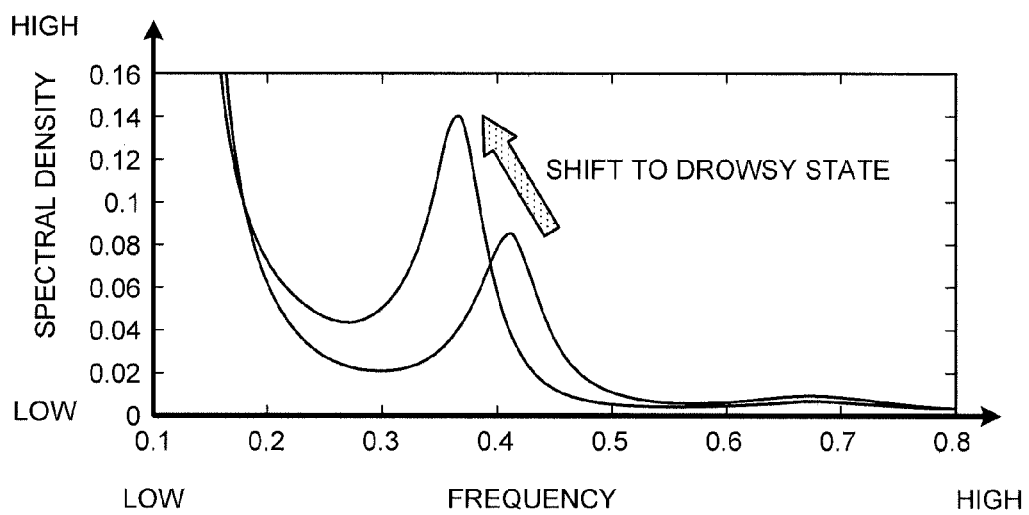
FIG. 9A is a diagram illustrating a change during a shift to a drowsy state in the second embodiment.

Plotting on the consciousness level determination graph by using the method corresponding to the comparison results will be described. As described above, the consciousness level determination adjuster 260 allocates the drowsiness levels to the consciousness level determination graph such that the drowsiness level represents that the consciousness level decreases from the upper right area to the lower left area. The basis for this is the fact that, as depicted in FIG. 9A, the maximum frequency decreases and the maximum density increases as the consciousness level decreases and the drowsiness increases. In such a case, on the consciousness level determination graph, the plot position moves toward the lower left. FIG. 9A is a diagram illustrating changes during a shift to a drowsy state in the second embodiment.

Figure 9B:
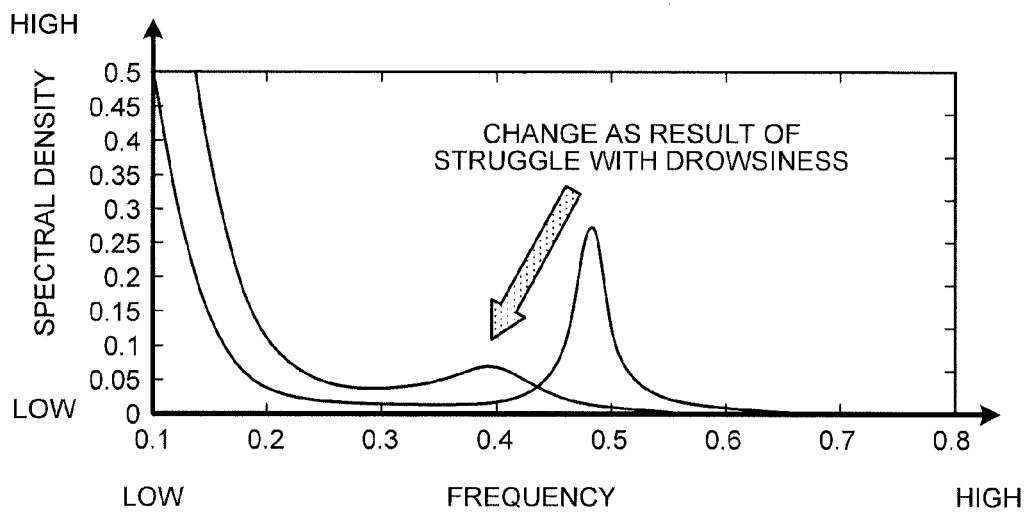
FIG. 9B is a diagram illustrating a change during a state of resisting drowsiness.

As illustrated in FIG. 9B, the more the subject is in a state of resisting drowsiness, i.e., in a state of trying not to sleep, the more the maximum frequency decreases, the maximum density decreases, and the magnitude difference relation decreases. FIG. 9B is a diagram illustrating changes in a state of resisting drowsiness. Specifically, in the state where the subject is trying not to sleep, even if the maximum frequency decreases, the maxim density does not increase. Presumably, this is because, in the state where the subject is trying not to sleep, the parasympathetic nerves are in a state in which they function unstably and the maximum frequency is not concentrated in a specific state.

Figure 10:
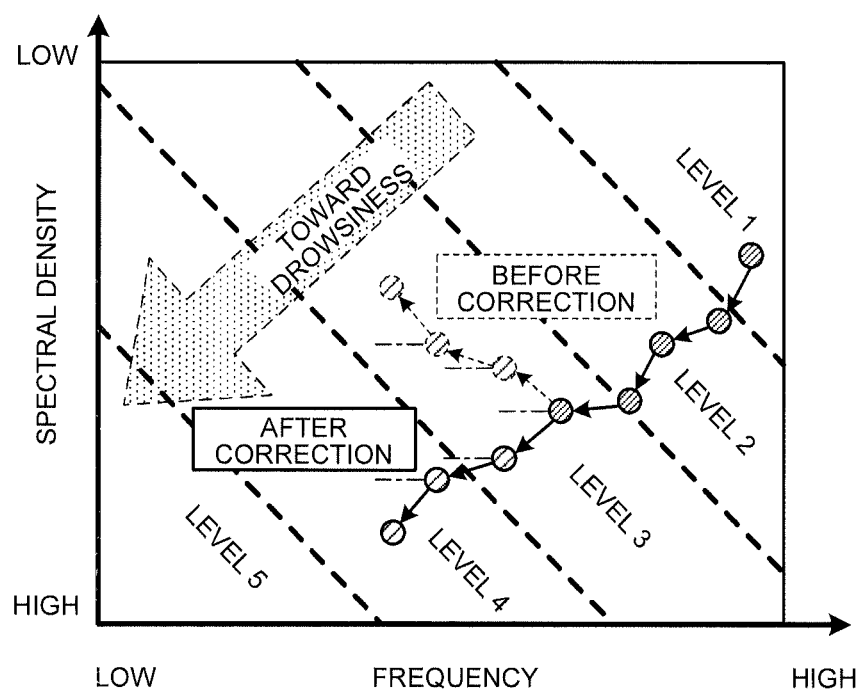
FIG. 10 is a diagram illustrating a plotting method used by the consciousness level determination adjuster of the second embodiment.

FIG. 10 is a diagram illustrating the method of plotting performed by the consciousness level determination adjuster of the second embodiment. As in the case of FIGS. 7 and 8, the vertical axis represents spectral density, the horizontal axis represents frequency, and combinations of maximum frequency and maximum density are plotted. When the state of FIG. 9B is plotted on FIG. 10, as illustrated using "before correction" in FIG. 10, the plot position moves toward the upper left in the consciousness level determination graph. As illustrated in FIG. 10, even if the plot position moves toward the upper left, the drowsiness level does not necessarily increase, i.e., in this state, the consciousness level determination unit 270 determines that the consciousness level is maintained.

In the state where a driver is trying not to sleep, there is a tendency that, when the driver stops trying not to sleep, the consciousness level suddenly decreases; therefore, it is desirable that the lower conspicuousness level in such a state be detected accurately. Thus, in the state where the driver is trying not to sleep, the plot position is corrected not such that the plot position moves toward the upper left but such that the plot position moves toward the lower left, as illustrated using the "after correction" in FIG. 10. As a way of correcting the plot position, it is possible, for example, to use the unchanged value of maximum frequency and set, to the corrected maximum density, a value obtained by adding the value of decrease from the old maximum density to the old maximum density. It is possible to use, as the old maximum density, the latest plot that follows a trend of the maximum frequency to reduce and the maximum density to increase, i.e., the plot just before the trend is shown of both the maximum density and the maximum frequency to decrease.

The correcting way is not limited to the above-described way. When a comparison result indicating that the subject is resisting drowsiness is obtained, the consciousness level determination adjuster 260 changes the determination reference such that the consciousness level with respect to a single detected value becomes lower compared to the case where other comparison results are obtained.

For example, when the received comparison results indicate that the received maximum frequency is equal to or less than the old maximum frequency, the received maximum density is not equal to or greater than the old density, and the received magnitude difference relation is not equal to or greater than the old magnitude difference relation, the consciousness level determination adjuster 260 corrects the plot position. In other words, in the state where the subject is trying not to sleep and the comparison results indicate that the maximum frequency and the maximum density both decrease and the magnitude difference relation decreases, the consciousness level determination adjuster 260 corrects the plot position. In contrast, when another comparison result is obtained, the consciousness level determination adjuster 260 performs plotting without correcting the plot position.

The consciousness level determination adjuster 260 outputs the consciousness level determination graph to the consciousness level determination unit 270.

The consciousness level determination unit 270 is connected to the consciousness level determination adjuster 260 and the output unit 280. The consciousness level determination unit 270 receives the consciousness level determination graph from the consciousness level determination adjuster 260 and determines a consciousness level from the consciousness level determination graph. In the example in FIG. 10, when the plots representing the maximum frequency and the maximum density shift toward the lower left in the consciousness level determination graph, the consciousness level determination unit 270 determines that the subject is shifting from a conscious state to a sleeping state.

For example, when comparison results are obtained that indicate that the maximum frequency decreases, the maximum density decreases, and the magnitude difference relation decreases compared to the combination extracted at the previous timing, the consciousness level determination unit 270 determines that the consciousness level decreases.

The consciousness level determination unit 270 outputs the result of the determination to the output unit 280. For example, the fact that there is a decrease in the consciousness level is output.

The output unit 280 is connected to the consciousness level determination unit 270. The output unit 280 corresponds to a monitor (or a display or a touch panel) and a speaker. Upon receiving the determination result from the consciousness level determination unit 270, the output unit 280 outputs the received determination result to the subject. For example, the information indicating that the consciousness level decreases is output to the user.

Figure 11:
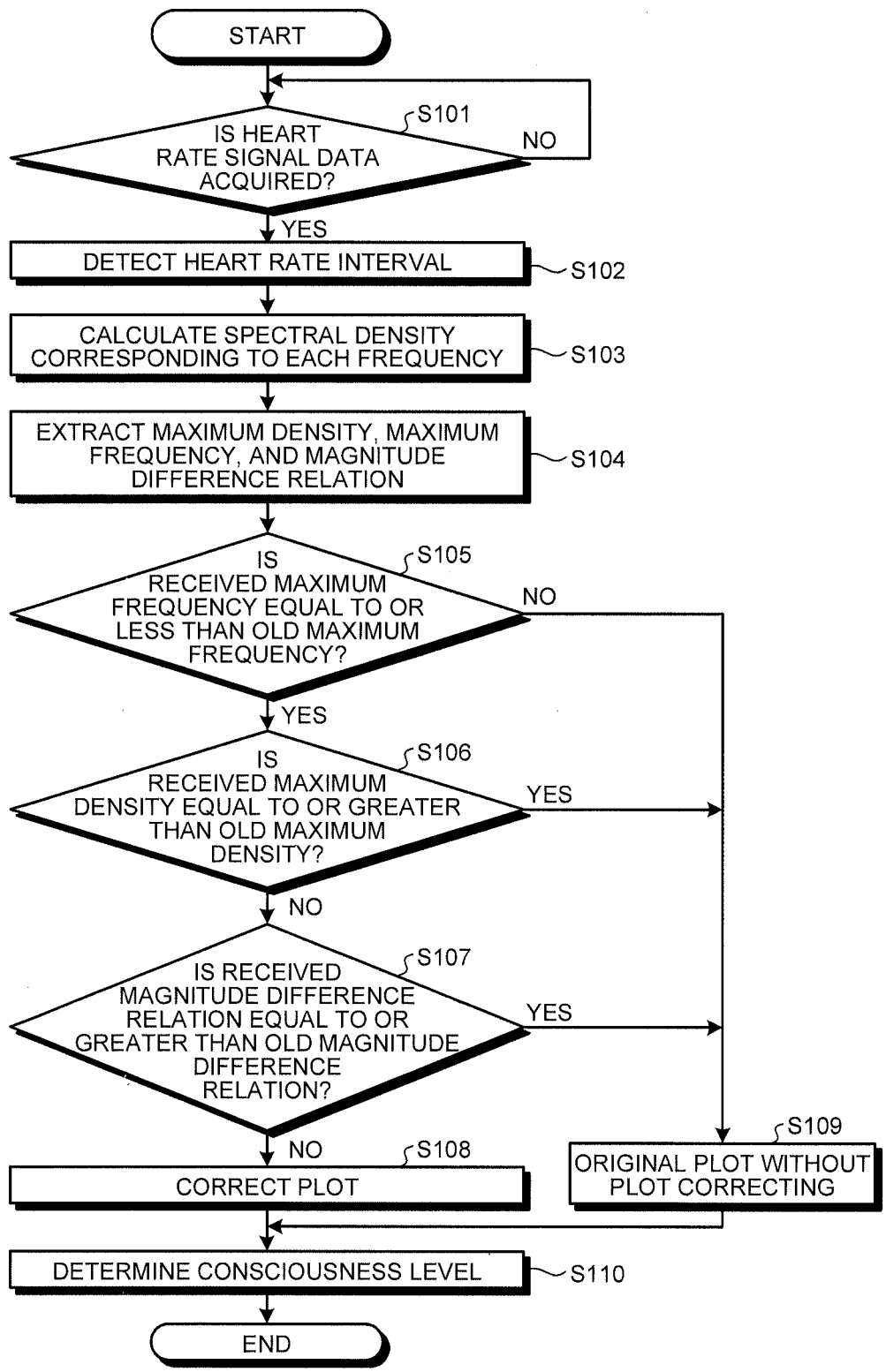
FIG. 11 is a flowchart illustrating an example of a flow of processes performed by the consciousness level determination apparatus according to the second embodiment.

Process Performed by Consciousness Level Determination Apparatus According to the Second Embodiment The processes performed by the consciousness level determination apparatus 100 according to the second embodiment will be described using FIG. 11. FIG. 11 is a flowchart illustrating an example of the flow of the processes performed by the consciousness level determination apparatus according to the second embodiment.

As depicted in FIG. 11, in the consciousness level determination apparatus 100, the heart rate detector 210 detects heart rate signal data (YES at S101), and the heart rate interval calculator 220 detects a heart rate interval (S102).

The spectrum calculator 230 calculates a spectral density corresponding to each frequency on the basis of the heart rate interval data (S103). The peak frequency calculator 240 then extracts a maximum density, a maximum frequency, and a magnitude difference relation (S104).

The peak waveform determination unit 250 compares the received maximum frequency and an old maximum frequency and determines whether the received maximum frequency is equal to or less than the old maximum frequency (S105). The peak waveform determination unit 250 compares the received maximum density and an old maximum density and determines whether the received maximum density is equal to or greater than the old maximum density (S106). The peak waveform determination unit 250 compares the received magnitude difference relation and an old magnitude difference relation and determines whether the received magnitude difference relation is equal to or greater than the old magnitude difference relation (S107).

A case will be described where the received maximum frequency is equal to or less than the old maximum frequency (YES at S105), the received maximum density is not equal to or greater than the old maximum density (NO at S106), and the received magnitude difference relation is not equal to or greater than the old magnitude difference relation (NO at S107). In this case, the consciousness level determination adjuster 260 corrects the plot (S108). In other words, the consciousness level determination adjuster 260 corrects the plot position when a comparison result is obtained that indicates that the subject is trying not to sleep and the maximum frequency and the maximum density decrease and the magnitude difference relation decreases.

A case will be described here where the received maximum frequency is not equal to or less than the old maximum frequency (NO at S105), the received maximum density is equal to or greater than the old maximum density (YES at S106), and the received magnitude difference relation is equal to or greater than the old magnitude difference relation (YES at S107). In this case, the consciousness level determination adjuster 260 does not correct the plot (S109). In other words, the consciousness level determination adjuster 260 performs plotting at the original position.

The consciousness level determination unit 270 determines a consciousness level by using a consciousness level determination graph that is created by the consciousness level determination adjuster 260 (S110). Specifically, when the plot representing the maximum frequency and the maximum density shifts toward the lower left in the consciousness level determination graph, the consciousness level determination unit 270 determines that the subject is shifting from a conscious state to a sleeping state.

Effects of Second Embodiment

As described above, according to the second embodiment, the consciousness level determination apparatus 100 calculates a spectral density of each frequency by calculating a heart rate interval from a heart rate signal of a subject and performing a frequency analysis on the calculated heart rate interval. The consciousness level determination apparatus 100 then extracts a combination of a maximum density, a maximum frequency, and a magnitude difference relation at each predetermined timing. The consciousness level determination apparatus 100 then compares the maximum density, the maximum frequency, and the magnitude contained in the extracted combination with a maximum density, a maximum frequency, and a magnitude contained in a combination extracted at a previous timing. The consciousness level determination apparatus 100 determines a consciousness level on the basis of a determination reference that is determined by the result of the comparison.

Specifically, as a result of the comparison, the consciousness level determination apparatus 100 determines that the consciousness level decreases when, compared to the combination extracted at the previous timing, the maximum frequency decreases, the maximum density decreases, and the magnitude difference relation decreases. As a result, even in the state where the subject feels drowsy but is resisting falling asleep, a consciousness level can be determined appropriately. Specifically, in the state where the subject feels drowsy but is resisting falling asleep, it can be determined not that the consciousness level has no change but that the consciousness level decreases.

By estimating the consciousness level of the driver who is driving and understanding the state with respect to the driver's drowsiness, the risk of a state of falling asleep can be determined with higher accuracy.

[c] Third Embodiment

The first embodiment and the second embodiment are described above. The present invention may be carried out in another embodiment in addition to the above-described first and second embodiments. The other embodiments will be described below.

For example, the consciousness level determination apparatus 100 may preciously store the way in which the drowsiness shifts in each drive taken by the driver and determine whether there are normal changes by comparing the current shift in the drowsiness of the subject with an old shift.

Figure 12:
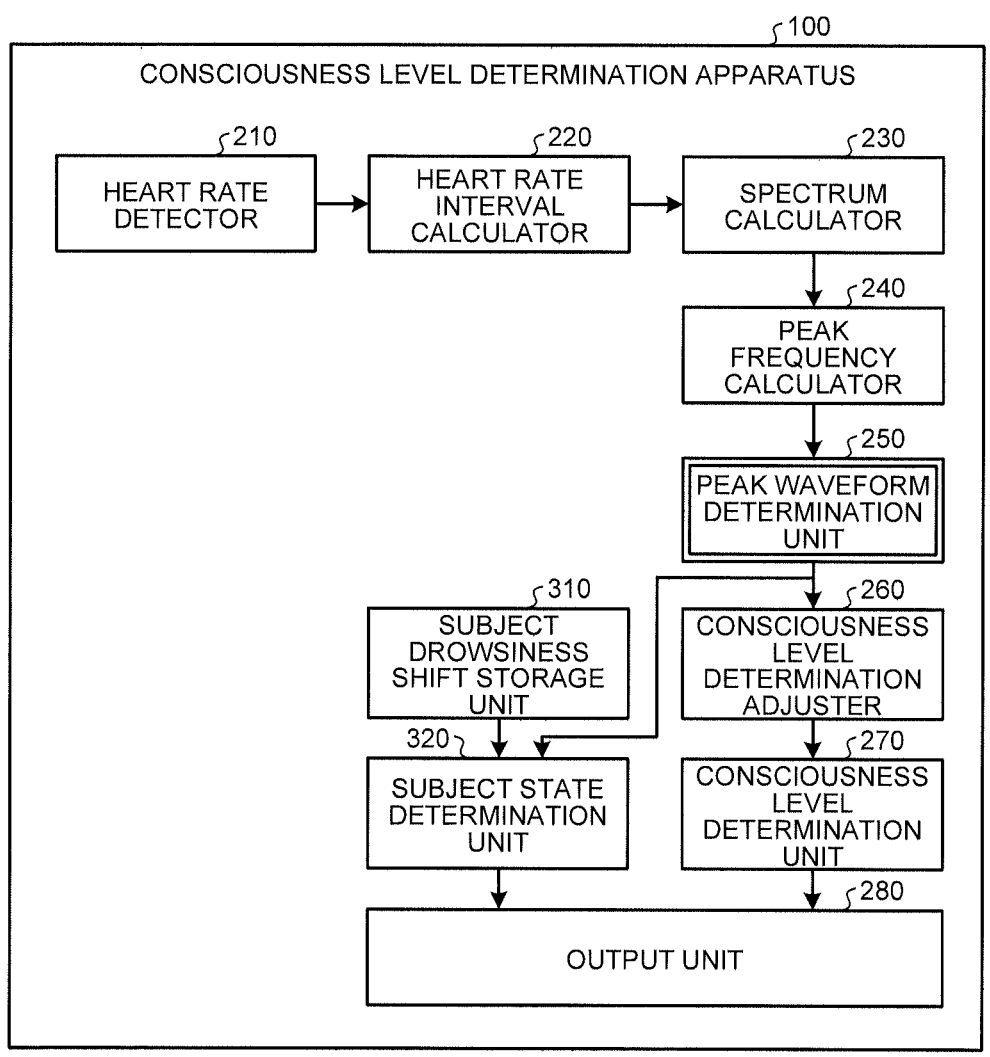
FIG. 12 is a block diagram illustrating an example of the configuration of the consciousness level determination apparatus that compares current and old shifts of drowsiness of the subject.

Specifically, as illustrated in FIG. 12, the consciousness level determination apparatus 100 includes a subject drowsiness shift storage unit 310 that stores the way in which the drowsiness shifts in each drive taken by the subject; and a subject state determination unit 320 that compares the current shift in drowsiness in the subject with an old shift. FIG. 12 is a block diagram illustrating an example of a configuration of the consciousness level determination apparatus that compares the current shift in drowsiness of the subject with the old shift.

The subject drowsiness shift storage unit 310 is connected to the subject state determination unit 320. The subject drowsiness shift storage unit 310 preciously stores the way in which the drowsiness shifts in each drive taken by the subject. For example, the subject drowsiness shift storage unit 310 stores, as the way in which the drowsiness shifts in each drive taken by the subject, the time to increase the drowsiness level, the drowsiness level when the state of resisting drowsiness is detected, and the time for which a resistance against drowsiness is performed.

The subject state determination unit 320 is connected to the subject drowsiness shift storage unit 310 and the peak waveform determination unit 250. The subject state determination unit 320 receives the received maximum frequency, the received maximum density, and the comparison results from the peak waveform determination unit 250. The subject state determination unit 320 determines whether the way in which the drowsiness shifts is the same as the old way in which the drowsiness shifted, which is stored in the subject drowsiness shift storage unit 310.

If, for example, it is not the same as the old way in which the drowsiness shifted, the subject state determination unit 320 outputs the fact to the output unit 280 and the output unit 280 outputs the fact to the subject. A case will be described where, for example, a subject that is shifting to sleep while taking an action of resisting the drowsiness once shifts to sleep without taking an action of resisting the drowsiness. In this case, the subject state determination unit 320 determines that there is a possibility of fatigue or sickness, outputs information giving advice to stop driving and have a rest to the output unit 280 and the output unit 280 outputs the information to the subject.

State Determination Process and Risk Determination Process

For example, the consciousness level determination apparatus 100 may perform a state determination process for determining the state of the subject and a risk determination process for determining the risk of drowsiness. For example, at S110 in FIG. 11, the consciousness level determination unit 270 may not only determine a consciousness level but further perform the state determination process and the risk determination process.

Figure 15:
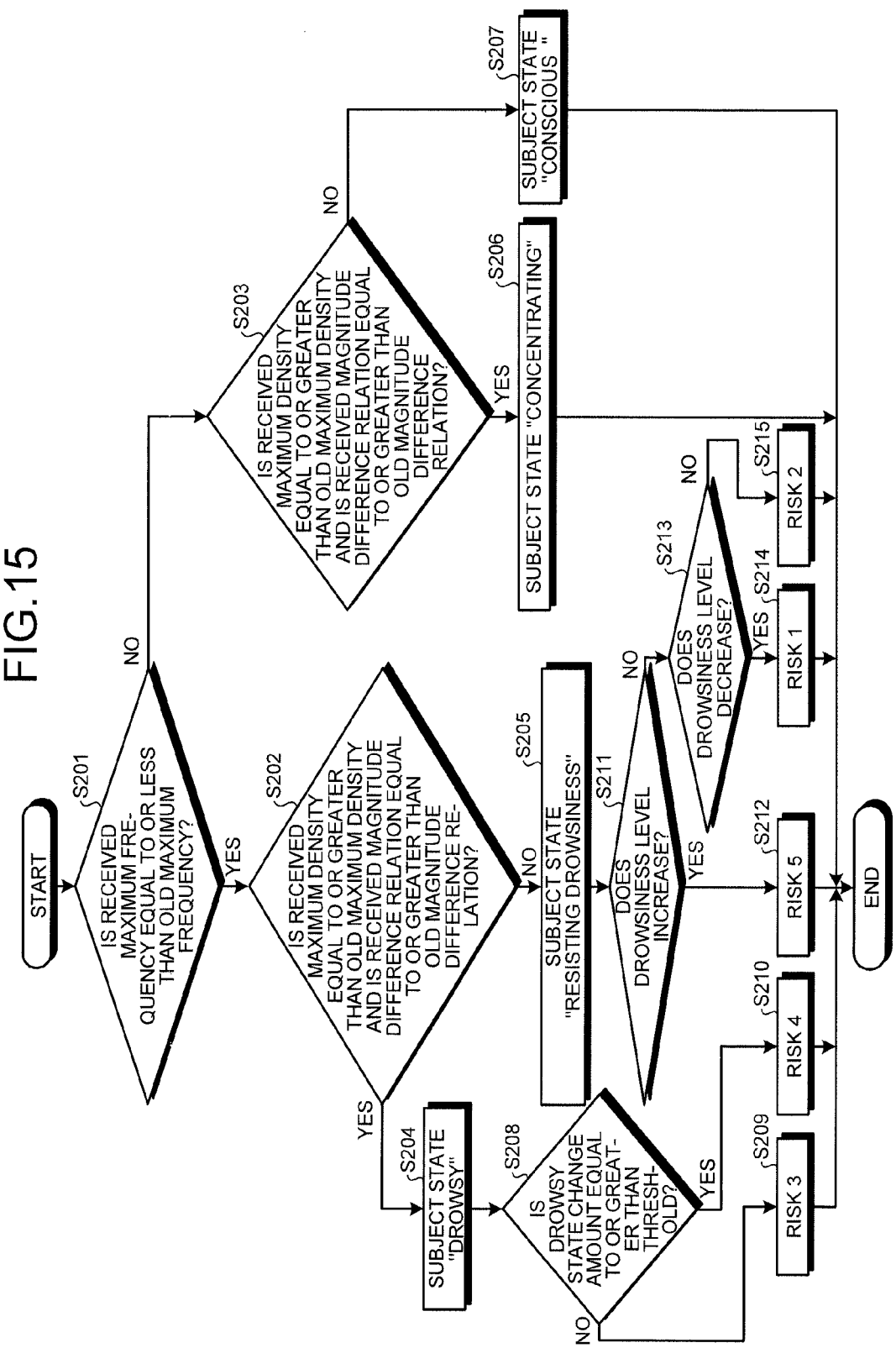
FIG. 15 is a flowchart illustrating an example of a flow of processes of a state determination process and a risk determination process.

Using FIG. 5, a case will be described in which the consciousness level determination unit 270 further performs the state determination process and the risk determination process at S110 in FIG. 11. FIG. 15 is a flowchart illustrating an example of the process flow of the state determination process and the risk determination process. The consciousness level determination unit 270 performs the series of processes described below in FIG. 15, for example, after S110 in FIG. 11, which is the process in which a consciousness level is determined, or performs the series of processes in parallel with the process for determining a consciousness level. Among the series of processes described below, S201 to S207 are processes relating to the state determination process and S208 to S215 are processes relating to the risk determination process.

As illustrated in S201 to S207, the consciousness level determination unit 270 performs the state determination process. For example, the consciousness level determination unit 270 determines whether the received maximum frequency is equal to or less than an old maximum frequency (S201). The consciousness level determination unit 270 further determines whether a received maximum density is equal to or greater than an old maximum density and a received magnitude difference relation is equal to or greater than an old magnitude difference relation (S202 and S203).

A case will be described in which the consciousness level determination unit 270 determines that the received maximum frequency is equal to or less than the old maximum frequency (YES at S201). When the consciousness level determination unit 270 determines that the received maximum density is equal to or greater than the old maximum density and the received magnitude difference relation is equal to or greater than the old magnitude difference relation (YES at S202), it determines that the state of the subject is "drowsy" (S204). In other words, when the maximum frequency decreases, the maximum density increases, and the magnitude difference relation increases, it is assumed that the drowsiness of the subject is increasing. Thus, the consciousness level determination unit 270 determines that the subject is in the sleep state or is shifting to the sleep state.

In contrast, when the consciousness level determination unit 270 does not determine that the received maximum density is equal to or greater than the old maximum density and the received magnitude difference relation is equal to or greater than the old magnitude difference relation (NO at S202), it determines that the state of the subject is "resisting drowsiness" (S205). In other words, when the maximum frequency decreases, the maximum density decreases, and the magnitude difference relation decreases, it is assumed that the subject is in the state of trying to reduce the increasing drowsiness and thus the consciousness level determination unit 270 determines that the subject is in a state of resisting drowsiness.

A case will be described in which the consciousness level determination unit 270 does not determine that the received maximum frequency is equal to or less than the old maximum frequency (NO at S201). When the consciousness level determination unit 270 determines that the received maximum density is equal to or greater than the old maximum density and that the received magnitude difference relation is equal to or greater than the old magnitude difference relation (YES at S203), it determines that the state of the subject is "concentrating" (S206). In other words, when the maximum frequency increases, the maximum density increases, and the magnitude difference relation increases, it is assumed that the subject is concentrating on driving and thus it is determined that the subject is in a state of concentrating.

In contrast, when the consciousness level determination unit 270 does not determine that the received maximum density is equal to or greater than the old maximum density and that the received magnitude difference relation is equal to or greater than the old magnitude difference relation (NO at S203), it determines that the state of the subject is "conscious" (S207). In other words, for example, when the maximum frequency increases, the maximum density decreases, and the magnitude difference relation decreases, it is assumed that the subject is changing toward consciousness and thus it is determined that the subject is in the conscious state or is in a state of shifting from the sleep state to the conscious state.

The state determination process performed by the consciousness level determination unit 270 will be summarized here. A decrease in the maximum frequency indicates that the consciousness level decreases. When the maximum density increases or the magnitude difference relation increases, the consciousness level determination unit 270 determines that the subject is in the drowsy state. When the maximum density decreases or the magnitude difference relation decreases, the consciousness level determination unit 270 determines that the subject is resisting drowsiness.

An increase in the maximum frequency indicates that the consciousness level of the subject increases. When the maximum density increase or the magnitude difference relation increases, the consciousness level determination unit 270 determines that the subject is in the concentrating state. When the maximum density decreases or the magnitude difference relation decreases, the consciousness level determination unit 270 determines that the subject is in the conscious state.

As illustrated in S208 to S215 in FIG. 15, when the state of the subject is "drowsy" or "resisting drowsiness", the consciousness level determination unit 270 performs the risk determination process on the basis of the conscious state of the subject. An example in which there are five levels of risk will be described. However, the present invention is not limited to this. There may be four levels of risk or six or more levels of risk. A case will be described below where the risk increases from Risk 1 to Risk 5. In other words, for example, Risk 1 denotes the state of least risk and Risk 5 denotes the state of most risk.

A case will be described in which the consciousness level determination unit 270 determines that the state of the subject is "drowsy" (S204). The consciousness level determination unit 270 determines whether the amount of change in the drowsy state is equal to or greater than a threshold (S208). For example, the consciousness level determination unit 270 determines whether the drowsiness level increases by one. The case in which a determination is made by using the drowsiness level is shown as an example, but the present invention is not limited to this and the user can set an arbitrary threshold. When the consciousness level determination unit 270 does not determine that the amount of change toward drowsiness is equal to or greater than the threshold (NO at S208), it is assumed that the drowsiness increases and thus the consciousness level determination unit 270 determines that the risk is "3" (S209). In contrast, when the consciousness level determination unit 270 determines that the amount of change toward drowsiness is equal to or greater than the threshold (YES at S208), it is assumed that the drowsiness increases rapidly and thus the consciousness level determination unit 270 determines that the risk is "4" (S210).

A case will be described in which the consciousness level determination unit 270 determines that the state of the subject is "resisting drowsiness" (S205). The consciousness level determination unit 270 determines whether the drowsiness level of the subject after a predetermined time is higher than the current drowsiness level (YES at S211). When the consciousness level determination unit 270 determines that the drowsiness level increases (YES at S211), there is no effect to be conscious even with an action of resisting drowsiness to stay awake and it is assumed that this is the state of most risk. Thus, the consciousness level determination unit 270 determines that the risk is "5" (S212).

When the consciousness level determination unit 270 does not determine that the drowsiness level of the subject after the predetermined time is higher than the current drowsiness level (NO at S211), it determines whether the drowsiness level of the subject is lower than the current drowsiness level (S213). When the consciousness level determination unit 270 determines whether the drowsiness level of the subject is lower than the current drowsiness level (YES S213), because it is assumed that there is an effect of an action for staying awake and there is a change toward consciousness, the consciousness level determination unit 270 determines that the risk is "1" (S214). In contrast, when the consciousness level determination unit 270 does not determine that the drowsiness level of the subject decreases (NO at S213), it determines that the risk is "2" (S215). In other words, when the drowsiness level does not change, it is assumed that the drowsiness does not increase and the state can be maintained because of the action for staying awake, and the consciousness level determination unit 270 determines that the risk is "2".

By performing the state determination process and the risk determination process as described above, not only a consciousness level but also a state of the subject or risk can be determined.

Detection of Heart Rate

In the second embodiment, a case is described in which the heart rate detector 210 detects a heart rate signal from the potential difference between the electrodes. However, the present invention is not limited to this. For example, it is satisfactory if the heart rate detector 210 can capture the heartbeat or beats per minute of a subject. For example, the heart rate detector 210 may be an electrocardiograph, a sphygmograph, or a heart sound sensor. Alternatively, for example, an ear clip sensor that captures the heartbeat may be used.

Output Result

In the second embodiment, a case is described in which the output unit 280 outputs the result of the determination made by the consciousness level determination unit 270. However, the present invention is not limited to this. For example, the consciousness level determination graph may be output.

Combination with Automotive Navigation System

The consciousness level determination apparatus 100 may be combined with an automotive navigation system that is installed in an automobile. For example, the environment of an automobile in which a subject easily enters (or does not easily enter) the conscious state can be easily analyzed by storing the position of the automobile and the road condition, which can be acquired from the automotive navigation system, in association with a representative frequency and a representative spectral density. The consciousness level determination graph may be output to the monitor of the automotive navigation system. If the screen of the car navigation system can display two screens facing the driver's set side and the passenger's seat side, a graph that is generated by using the consciousness level determination graph may be displayed only on the screen on the passenger seat side. By displaying the graph only on the screen on the passenger seat side, the discomfort of the driver who is a subject can be reduced and comfort can be given to the passenger in the passenger seat.

Case in which Multiple Maxima are in HF Component

For example, in the second embodiment, a case is described in which the peak frequency calculator 240 receives spectral density data in which there is one maximum in the HF component and extracts one combination of a maximum density, a maximum frequency, and a magnitude difference relation. However, as depicted in FIG. 5, spectral density data in which there are multiple maxima in the HF component may be received.

In such a case, the peak frequency calculator 240 may calculate a maximum frequency, a maximum density, and a magnitude difference relation for each of the maxima. Alternatively, the calculation may be performed only for a maximum with the greatest spectral density among the maxima in the HF component.

Figure 13A:
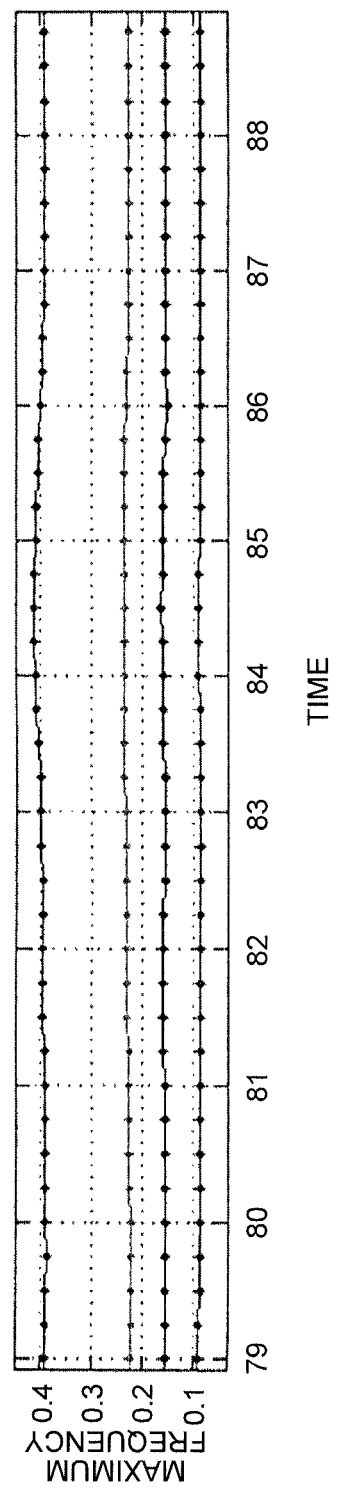
FIG. 13A is a diagram of changes in maximum frequency in the time series in the second embodiment.

For example, when the peak frequency calculator 240 calculates a maximum frequency and a maximum density for each of the multiple maxima, as illustrated in FIGS. 13-1 to 13-2, changes in maximum frequency or maximum density can be obtained in the time series for each of the multiple maxima. FIG. 13A is a diagram of changes in the maximum frequencies in the time series in the second embodiment. FIG. 13B is a diagram of changes in the maximum density in the time series in the second embodiment. The horizontal axis in FIGS. 13-1 and 13-2 represents the elapse of time. The vertical axis in FIG. 13A represents maximum frequency and the vertical axis in FIG. 13B represents maximum density.

Drowsiness Level

For example, in the second embodiment, the case is described in which the drowsiness levels are "1" to "5". However, the present invention is not limited to this. For example, the drowsiness levels may be from "1" to "100".

System Configuration

Among the processes described in the embodiments, the processes that are described as those automatically performed may be entirely or partially manually performed. Alternatively, the processes that are described as those performed manually may be entirely or partially automatically performed using a well-known method. The process procedures, control procedures, specific names, and information including various types of data and parameters that are illustrated in the specification and the drawings (for example, FIG. 1 to FIG. 13) may be changed arbitrarily unless otherwise noted.

All the components of the consciousness level determination apparatus 100 illustrated in the drawings are functional ideas and do not need to be physically configured as illustrated in the drawings. In other words, the specific modes of separation or integration of each device are not limited to those illustrated in the drawings and the elements may be configured in a way that they are entirely or partially separated or integrated functionally or physically on an arbitrary basis in accordance with various loads or how they are used. For example, if this is described using the example in FIG. 2, the heart rate detector 210 may be an independent device and the consciousness level determination apparatus 100 may receive a heart rate signal from the heart rate detector 210, which is an independent device.

Computer

Figure 14:
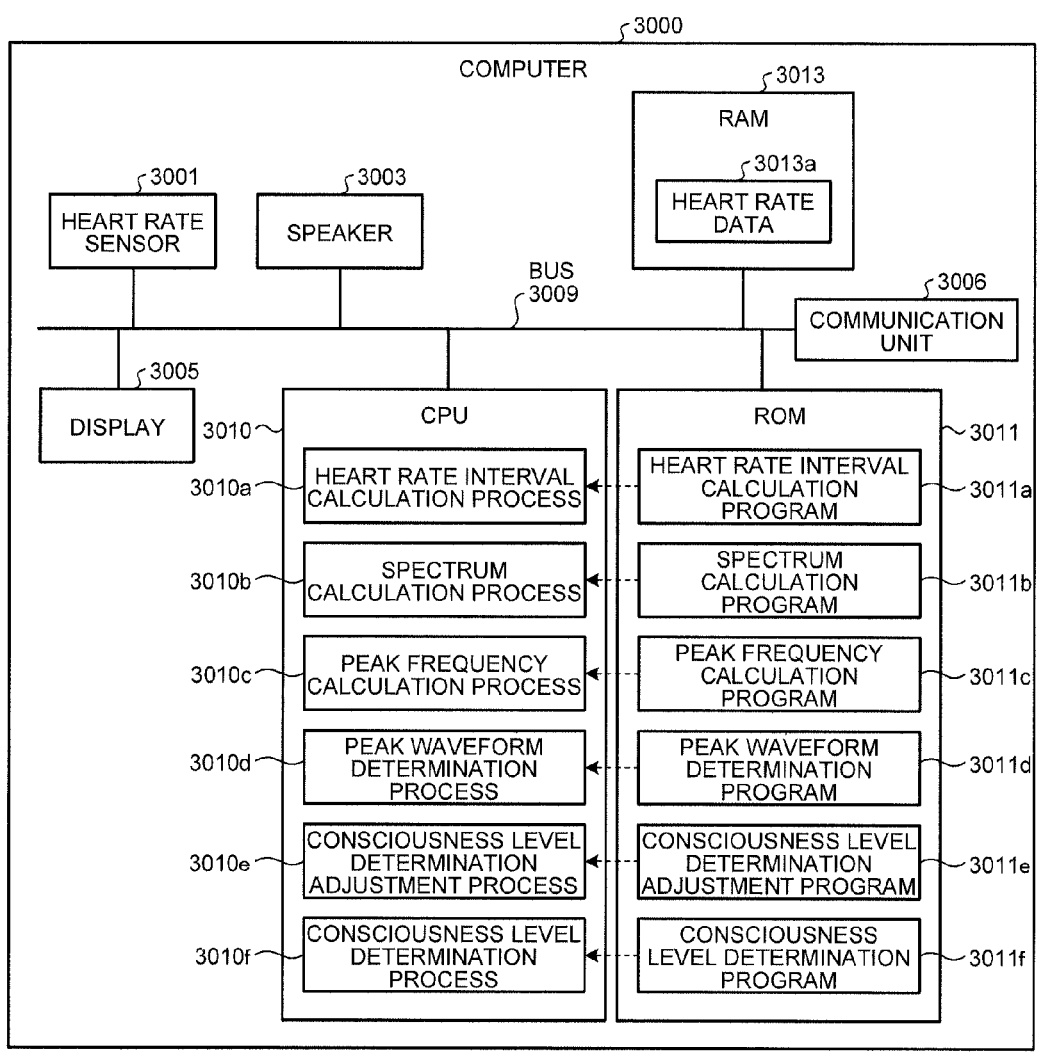
FIG. 14 is a diagram illustrating an example of a computer that executes a consciousness level determination program according to the second embodiment.

Various types of processes that are described in the above-described embodiments can be achieved by executing a prepared program using a computer, such as a personal computer or a work station. An example of a computer that executes a consciousness level determination program that achieves the same functions as those of the above-described embodiments will be described using FIG. 14. FIG. 14 is a diagram illustrating an example of a computer that executes the consciousness level determination program according to the second embodiment.

As illustrated in FIG. 14, a computer 3000 of the first embodiment is configured by connecting, via a bus 3009, includes a heart rate sensor 3001, a speaker 3003, a display 3005, a communication unit 3006, a CPU 3010, a ROM 3011, a RAM 3013. The heart rate sensor 3001 corresponds to the heart rate detector 210. The speaker 3003, the display 3005, and the communication unit 3006 correspond to the output unit 280.

The ROM 3011 previously stores a control program for performing the same functions as those of the heart rate interval calculator 220, the spectrum calculator 230, the peak frequency calculator 240, the peak waveform determination unit 250, the consciousness level determination adjuster 260, and the consciousness level determination unit 270. A heart rate interval calculation program 3011a, a spectrum calculation program 3011b, a peak frequency calculation program 3011c, and a peak waveform determination program 3011d are previously stored in the ROM 3011. A consciousness level determination adjustment program 3011e and a consciousness level determination program 3011f are previously stored in the ROM 3011. The programs 3011a to 3011f may be appropriately integrated or separated, as are the components of the consciousness level determination apparatus 100 in FIG. 2.

The CPU 3010 reads the programs 3011a to 3011f from the ROM 3011 and executes them. Accordingly, as illustrated in FIG. 14, the programs 3011a to 3011f serve as a heart rate interval calculation process 3010a, a spectrum calculation process 3010b, a peak frequency calculation process 3010c, a peak waveform determination process 3010d, a consciousness level determination adjustment process 3010e, and a consciousness level determination process 3010f. The processes 3010a to 3010f corresponds to the heart rate interval calculator 220, the spectrum calculator 230, the peak frequency calculator 240, the peak waveform determination unit 250, the consciousness level determination adjuster 260, and the consciousness level determination unit 270, respectively.

The CPU 3010 executes the consciousness level determination program by using heart rate data 3013a that is stored in the RAM 3013.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A method of determining a consciousness level comprising:

detecting an amplitude peak of a heart rate signal of a subject;

calculating, using a processor, a heart rate interval between the amplitude peak of the heart rate signal and a previously detected amplitude peak of the heart rate signal;

calculating, using the processor, a relation between frequency and spectral density by performing a frequency analysis on the heart rate interval;

extracting, using the processor, upon detecting the amplitude peak of the heart rate signal at the detecting step, a combination of a maximum density that is a maximum among spectral densities that are calculated at the calculating a relation between frequency and spectral density step, a maximum frequency that is a frequency corresponding to the maximum density, and a magnitude difference relation that represents a difference between the maximum density and spectrum densities which correspond to frequencies adjoined to the maximum frequency;

comparing, using the processor, the maximum frequency, the maximum density, and the magnitude difference relation to a maximum frequency, a maximum density, and a magnitude difference relation that are contained in a combination extracted at a previous timing of the detecting step;

plotting, using the processor, the combination of the extracted maximum frequency and the extracted maximum density as a position on a consciousness level determination graph where the ordinate represents spectral density and abscissa represents frequency;

dividing, using the processor, the area of the consciousness level determination graph, and allocating the divided areas with drowsiness levels;

correcting, using the processor, the plotted position not such that the plotted position moves toward a positive end of the ordinate but such that the plot position moves toward an origin of the consciousness level determination graph; and determining, using the processor, the consciousness level by comparing the plotted extracted combination of maximum frequency and maximum density to the plotted combination extracted at the previous timing, where decreases in maximum frequency and maximum density of the extracted combination in comparison to the combination extracted at the previous timing indicates increasing drowsiness, and comparing the magnitude difference relation to the magnitude difference relation extracted at the previous timing, where decreases in the magnitude difference relation in comparison to the magnitude difference relation at the previous timing indicates the increasing drowsiness; and outputting the determination to a driver through a monitor and a speaker if the determination indicates increasing drowsiness.

2. A consciousness level determination apparatus comprising:

a processor; and a memory, wherein the processor executes:

detecting an amplitude peak of a heart rate signal of a subject;

calculating a heart rate interval between the amplitude peak of the heart rate signal and a previously detected amplitude peak of the heart rate signal;

calculating a relation between frequency and spectral density by performing a frequency analysis on the heart rate interval;

extracting, upon detecting the amplitude peak of the heart rate signal at the detecting step, a combination of a maximum density that is a maximum among spectral densities that are calculated at the calculating a relation between frequency and spectral density step, a maximum frequency that is a frequency corresponding to the maximum density, and a magnitude difference relation that represents a difference between the maximum density and spectrum densities which correspond to frequencies adjoined to the maximum frequency;

comparing the maximum frequency, the maximum density, and the magnitude difference relation to a maximum frequency, a maximum density, and a magnitude difference relation that are contained in a combination extracted at a previous timing of the detecting step;

plotting the combination of the extracted maximum frequency and the extracted maximum density as a position on a consciousness level determination graph where the ordinate represents spectral density and abscissa represents frequency;

dividing the area of the consciousness level determination graph, and allocating the divided areas with drowsiness levels;

correcting the plotted position not such that the plotted position moves toward a positive end of the ordinate but such that the plot position moves toward an origin of the consciousness level determination graph; and determining the consciousness level by comparing the plotted extracted combination of maximum frequency and maximum density to the plotted combination extracted at the previous timing, where decreases in maximum frequency and maximum density of the extracted combination in comparison to the combination extracted at the previous timing indicates increasing drowsiness, and comparing the magnitude difference relation to the magnitude difference relation extracted at the previous timing, where decreases in the magnitude difference relation in comparison to the magnitude difference relation at the previous timing indicates the increasing drowsiness; and outputting the determination to a driver through a monitor and a speaker if the determination indicates increasing drowsiness.

3. The consciousness level determination apparatus according to claim 2, wherein the calculating the spectral density of each frequency calculates using an auto regressive model that represents a state at a certain time point by using a linear sum of old time series data extracted at timing of the detecting step.

4. The consciousness level determination apparatus according to claim 2, wherein the magnitude difference relation is a value of a width of a spectral waveform of the heart rate signal at a predetermined length "L" from a maximum.

5. The consciousness level determination apparatus according to claim 2, wherein the consciousness level is provided to an automobile navigation system, which alerts a driver of an automobile.

* * * * *